US012781216B2

(12) United States Patent
Gagnon et al.

(10) Patent No.: US 12,781,216 B2

(45) Date of Patent: Nov. 3, 2026

(54) REMOVAL OF RNA AND CONTAMINANTS FROM DNA PLASMID PREPARATIONS BY HYDROPHOBIC INTERACTION CHROMATOGRAPHY

(71) Applicant: Sartorius BIA Separations d.o.o., Ajdovšcina (SI)

(72) Inventors: Peter S. Gagnon, Las Vegas, NV (US); Rok Sekirnik, Ajdovšcina (SI); Klemen Bozic, Ajdovšcina (SI)

(73) Assignee: Sartorius BIA Separations d.o.o.q, Ajdovscina (SI)

( * ) Notice: Subject to any disclaimer, the term of this patent is extended or adjusted under 35 U.S.C. 154(b) by 715 days.

(21) Appl. No.: 18/029,817

(22) PCT Filed: Oct. 5, 2021

(86) PCT No.: PCT/EP2021/077428

§ 371 (c)(1),
(2) Date: Mar. 31, 2023

(87) PCT Pub. No.: WO2022/073995

PCT Pub. Date: Apr. 14, 2022

(65) Prior Publication Data

US 2023/0374487 A1 Nov. 23, 2023

(30) Foreign Application Priority Data

Oct. 5, 2020 (EP) .................................... 20200088

(51) Int. Cl.

*C12N 15/10* (2006.01)
*B01D 15/16* (2006.01)
*B01D 15/32* (2006.01)

(52) U.S. Cl.

CPC ......... *C12N 15/101* (2013.01); *B01D 15/166* (2013.01); *B01D 15/327* (2013.01)

(58) Field of Classification Search

CPC ... C12N 15/101; B01D 15/166; B01D 15/327
USPC ........................................................ 536/25.4
See application file for complete search history.

(56) References Cited

U.S. PATENT DOCUMENTS

| | | | |
|---|---|---|---|
| 7,307,148 B2 | 12/2007 | Bosquet-Gagnon et al. | |
| 10,023,608 B1 | 7/2018 | Ma et al. | |
| 10,172,953 B2 | 1/2019 | Schellenberger et al. | |
| 2004/0038393 A1* | 2/2004 | Duarte | C12N 15/87 435/320.1 |
| 2004/0157244 A1* | 8/2004 | Budahazi | C12N 15/101 536/25.4 |
| 2009/0047734 A1 | 2/2009 | Berg et al. | |
| 2010/0150961 A1 | 6/2010 | Vedvick et al. | |
| 2011/0129468 A1 | 6/2011 | Mccue et al. | |

FOREIGN PATENT DOCUMENTS

| | | | |
|---|---|---|---|
| CN | 1956998 | A | 5/2007 |
| CN | 102239177 | A | 11/2011 |
| CN | 104302408 | A | 1/2015 |
| WO | 00-73318 | A1 | 12/2000 |
| WO | 2007-114762 | A1 | 10/2007 |

OTHER PUBLICATIONS

Bo et al. Using a single hydrophobic-interaction chromatography to purify pharmaceutical-grade supercoiled plasmid DNA from other isoforms. Pharmaceutical Biology, 2013; 51(1): 42-48. (Year: 2013).*

Xia et al., "Evaluation of selectivity changes in HIC systems using a preferential interaction based analysis", Biotechnology and Bioengineering, vol. 87 No. 3, p. 354-363, (Aug. 5, 2004).

Office Action and Search Report from corresponding Chinese Patent Application No. 202180065039X dated Apr. 16, 2025.

Freitas et al., "Plasmid purification by hydrophobic interaction chromatography using sodium citrate in the mobile phase", Separation and Purification Technology, 65(1):95-104, (2009).

Iuliano et al., "Rapid analysis of a plasmid by hydrophobic-interaction chromatography with a non-porous resin", Journal of Chromatography A;972(1):77-86, (Sep. 27, 2002).

Urh et al., "A multimodal histamine ligand for chromatographic purification of plasmid DNA", Journal of Chromatography A, 1281:87-93, (2013).

International Search Report for corresponding Patent Application No. PCT/EP2021/077428 dated Jan. 12, 2022.

* cited by examiner

*Primary Examiner* — Yih-Horng Shiao

(74) *Attorney, Agent, or Firm* — Christensen, Fonder, Dardi, Busse; Diane E. Bennett; Peter S. Dardi

(57) ABSTRACT

A method is disclosed for manufacturing a purified pDNA preparation from a sample comprising pDNA and a contaminant, the method comprising the steps of:

Contacting the sample with a hydrophobic interaction chromatography (HIC) material in a solution comprising a kosmotropic salt in a concentration which forces the pDNA and contaminant to adsorb on the HIC material, Diluting the concentration of the kosmotropic salt in presence of a neutral salt subsequent to adsorbing of the pDNA on the HIC material, thereby Desorbing the pDNA from the HIC material, whereas the contaminant stays adsorbed by the continued presence of the neutral salt, and Obtaining the pDNA preparation.

Furthermore, a method is disclosed for preparing a sample to be subjected to the method of the invention or other purification methods, in particular anion exchange chromatography by exposing the sample to a neutral salt in the presence of a HIC material.

18 Claims, 3 Drawing Sheets

REMOVAL OF RNA AND CONTAMINANTS FROM DNA PLASMID PREPARATIONS BY HYDROPHOBIC INTERACTION CHROMATOGRAPHY

CROSS REFERENCE TO RELATED APPLICATIONS

This application is a National Stage filing of PCT Application No. PCT/EP2021/077428 filed Oct. 5, 2021, entitled "Improved Removal of RNA and Contaminants from DNA Plasmid Preparations by Hydrophobic Interaction Chromatography", which claims priority to European Patent application Ser. No. 20/200,088.1, filed Oct. 5, 2020.

The invention pertains to a method for manufacturing a purified pDNA preparation from a sample comprising pDNA and a contaminant.

BACKGROUND

DNA plasmids obtained by lysis of producer cells are universally contaminated with proteins, RNA, RNA-protein aggregates and DNA-protein-RNA aggregates. Hydrophobic interaction chromatography (HIC) is among the tools known for purification method for plasmid DNA (pDNA) [1]. A sample is applied to a HIC column in a solution containing a high concentration of a precipitating salt. The pDNA binds but so do contaminants. The column is eluted with a descending salt gradient. Good separation can be obtained among plasmid isoforms such as supercoiled (sc), open-circular (oc), and linear pDNA but RNA co-elutes with the desired scDNA to a significant degree. Fair separation of pDNA from host cell proteins, RNA-protein aggregates and DNA-protein-RNA aggregates is also achieved. The inability of HIC to fully remove the remaining contaminants is most often compensated by the combination of HIC with anion exchange chromatography (AEC).

SUMMARY OF THE INVENTION

It has been surprisingly discovered that removal of contaminants from pDNA preparations by HIC can be enhanced when eluting the column by reducing the concentration of a kosmotropic salt (first salt) in the presence of a neutral salt (second salt). The pDNA is recovered by reducing the concentration of the kosmotropic salt in the continued presence of the neutral salt. RNA, proteins, RNA-protein aggregates and DNA-protein-RNA aggregates remain bound to the column by the continued presence of the second salt. It is believed that the neutral salt forces contaminants to remain strongly bound to the hydrophobic column. This contrasts with the traditional approach of elution with a simple gradient created by reducing the concentration of a kosmotropic salt in the absence of a neutral salt, in which various contaminants co-elute with the pDNA. This approach reduces the amounts of contaminants in the pDNA fraction and changes the spectrum of contaminants remaining in the pDNA fraction so that combining the method of the invention with another chromatography method produces more highly purified pDNA, compared to combining HIC as usually performed with another chromatography method.

Subject matter of the invention is a method for manufacturing a purified pDNA preparation from a sample comprising pDNA and a contaminant, the method comprising the steps of:

Contacting the sample with a hydrophobic interaction chromatography (HIC) material in a solution comprising a kosmotropic salt in a concentration which forces the pDNA and contaminant to adsorb on the HIC material, Diluting the concentration of the kosmotropic salt in presence of a neutral salt subsequent to adsorbing of the pDNA on the HIC material, thereby Desorbing the pDNA from the HIC material, whereas the contaminant stays adsorbed by the continued presence of the neutral salt, and Obtaining the pDNA preparation.

The term "precipitating salt" represents a carryover from the field of protein chemistry, where certain salts are known to be effective for precipitation of proteins. Ammonium sulfate is an example. Other species, such as guanidinium hydrochloride are strong solubilizing agents that prevent precipitation. Some alts, such as sodium chloride have dramatically less ability to promote precipitation of proteins. The effects of various salts on protein solubility are known to correlate with their respective rankings in the Hofmeister series [2].

Salts that promote precipitation are commonly classified as kosmotropic or lyotropic salts. Salts that promote solubility are commonly classified as chaotropic salts. Salts of intermediate character such as sodium chloride are commonly classified as neutral salts.

The term "neutral salt" in this context is understood not to refer to the pH of the aqueous solution in which a salt is dissolved. Instead, the term neutral salt is understood as any salt in which the combined and averaged contributions of the cation and anion produce an effect that is neither chaotropic nor kosmotropic, in other words neutral. Typically, monovalent metallic halide salts and monovalent metallic acetate salts are recognized as neutral salts.

In an embodiment of the method of the invention the kosmotropic salt can be a salt that contains a kosmotropic anion, cation, or both, in particular selected from the group consisting of ammonium sulfate, sodium sulfate, potassium phosphate, sodium citrate, potassium citrate, and combinations thereof. Typically, the concentration of the kosmotropic salt may be in the range of from 1.0 M to 2.5 M, or 1.25 M to 2.25 M, or 1.5 M to 2.0, or 1.7 M to 1.9 M. Many kosmotropic salts are of limited used because of their low solubility in water. Sodium phosphate is an example. It saturates at about 0.8 M, which is too low for it to have utility for the method of the present invention or for any precipitation-based technology. Potassium phosphate has utility because it remains soluble at much higher concentrations In another embodiment of the method of the invention the neutral salt may be selected from the group consisting of sodium chloride, potassium chloride, lithium chloride, ammonium chloride, sodium acetate, potassium acetate, lithium acetate, ammonium acetate, and combinations thereof. Typically, the concentration of the neutral salt can be in the range of from 0.5 M to 5.0 M, or 0.75 M to 4.0 M, or 1.0 M to 3.0 M, or 1.25 M to 2.5 M, or 1.5 M to 2.0 M. In yet another embodiment of the method of the invention the sample can be a lysate of prokaryotic cells containing plasmid DNA.

In a further embodiment of the method of the invention the contaminant can be selected from the group consisting of proteins, RNA, RNA-protein aggregates, DNA-protein aggregates and DNA-protein-RNA aggregates.

In still another embodiment of the method of the invention the HIC material can be a polymer bearing a hydrophobic ligand.

In a further embodiment of the method of the invention the hydrophobic ligand can be of an aromatic character, such as a phenyl and/or benzyl ligand; or of an alkyl character such as, a butyl, a hexyl, and/or octyl ligand or combinations thereof.

In another embodiment of the method of the invention the HIC material can be arranged in a chromatographic column In one embodiment, the method of the invention is a single method for removing contaminants from pDNA. A further embodiment of the present invention is a pre-purification method for preparing a sample to be subjected to other purification methods, in particular anion exchange chromatography. In particular, if the pre-purification method is employed the neutral salt can be lithium chloride or calcium chloride. In another embodiment, the method of the invention is a post-purification method for enhancing the purity of pDNA prepared by an alternative method, in particular anion exchange chromatography.

In an embodiment of the pre-purification method of the invention, the HIC material can be a hydrophobic depth filtration material, or a column packed with porous hydrophobic particles or nanofibers.

In another embodiment of the pre-purification method of the invention a kosmotropic salt may be added to the sample. In a closely related variant, the kosmotropic salt may be added as a liquid concentrate. In one such embodiment, the addition may be mediated by a mixing device to quickly achieve a homogenous mixture. In one such embodiment, the mixing may occur immediately before the mixture comes into contact with a HIC column to minimize formation of precipitates prior to the sample contacting the column.

In another embodiment of the pre-purification method of the invention the sample can be diluted with water or a low-conductivity buffer to prepare the sample for anion exchange chromatography.

In an embodiment of the post-purification method of the invention, the pDNA eluted from an anion exchanger, and still containing the neutral salt used to elute it from the anion exchanger, may be combined with a kosmotropic salt to mediate binding of the pDNA to a HIC column. As a general matter, this approach is less complicated and supports smoother overall process flow than the pre-purification method of the invention.

DETAILED DESCRIPTION OF THE INVENTION

Figure 1:
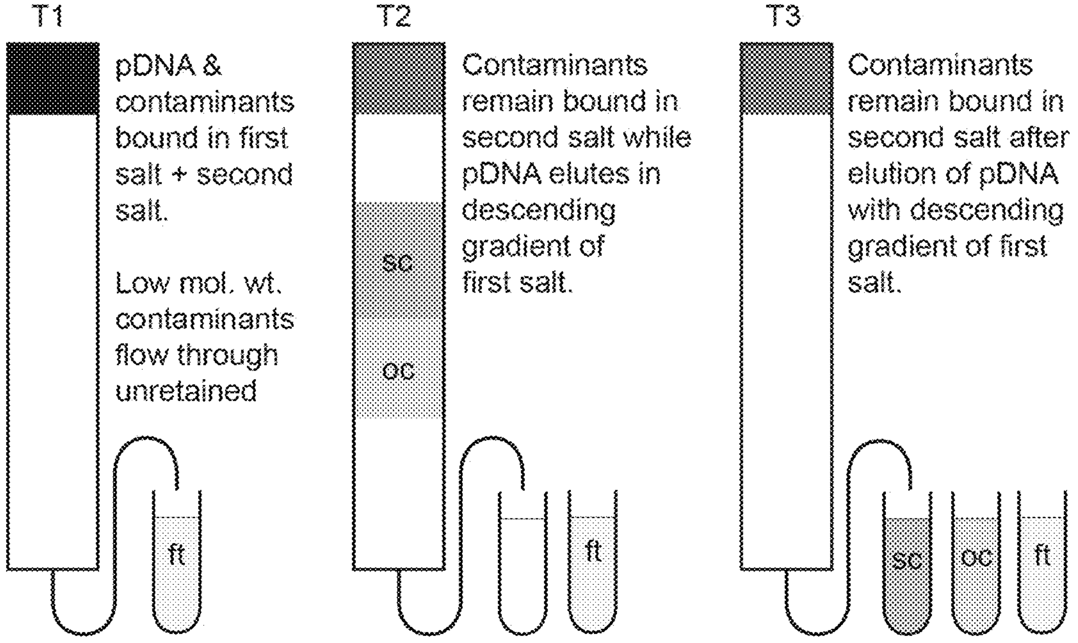
FIG. 1 depicts the stages of the method of the invention.

In some embodiments, the sample to be processed by the method of the invention is a filtered bacterial lysate containing plasmid DNA (pDNA). In some such embodiments, the bacterial host is *Escherichia coli*. In other embodiments, the sample to be processed by the method of the invention is a filtered pDNA-containing bacterial lysate that has been treated with calcium chloride to precipitate a portion of the RNA. In other embodiments, the sample to be processed by the method of the invention is prepared for chromatography by another method. In other embodiments, the sample to be processed by the method of the invention is partially purified. In other embodiments, the sample is substantially purified supercoiled plasmid DNA still contaminated with proteins, RNA, and/or DNA-protein-RNA aggregates in any amounts or relative proportions. In other embodiments, a partially purified pDNA to be processed by the method of the invention was partially purified by anion exchange chromatography.

In some embodiments, a HIC material used to practice the method of the invention is a polymer bearing hydrophobic ligands. The HIC ligands may be of an aromatic character, of an alkyl character, or of mixed character. Examples of aromatic HIC media include phenyl and benzyl media. Examples of alkyl HIC media include butyl, hexyl, and octyl media. Both types are used for purification of pDNA and both are widely available commercially worldwide in a variety of physical formats. Such formats include columns packed with porous particles, monoliths, membranes, and nanofibers, among others, employed in a chromatography device to facilitate the practice chromatography, usually referred to as a column.

In some embodiments, the kosmotropic salt is ammonium sulfate, or sodium sulfate, or potassium phosphate, or sodium citrate, or potassium citrate, or another kosmotropic salt. In one such embodiment where the kosmotropic salt is ammonium sulfate, the concentration of ammonium sulfate used to bind the DNA to the HIC column may be in the range of 1.0 M to 2.5 M, or 1.25 M to 2.25 M, or 1.5 M to 2.0, or 1.7 M to 1.9 M, depending on the hydrophobicity of the HIC column. It is well known in the art how to determine the concentration of a kosmotropic salt to achieve binding of pDNA to a HIC column. As a general matter, the stronger the hydrophobicity of the column, the lower the concentration of salt required to achieve the desired effect.

In some embodiments, the neutral salt is sodium chloride, or potassium chloride, or lithium chloride, or ammonium chloride, or sodium acetate, or potassium acetate, or lithium acetate, or ammonium acetate, or another neutral salt. In one such embodiment where the neutral salt is sodium chloride, the concentration of sodium chloride used to maintain binding of RNA and host cell DNA-protein-RNA aggregates to the HIC column may be in the range of 0.5 M to 5.0 M, or 0.75 M to 4.0 M, or 1.0 M to 3.0 M, or 1.25 M to 2.5 M, or 1.5 M to 2.0 M depending on the hydrophobicity of the HIC column. As with the kosmotropic salt, it is well known in the art how to determine the appropriate salt concentration.

Persons of experience in the art will recognize the benefit of maintaining ionic continuity among salt-containing buffers to avoid spontaneous precipitation of salts due to low solubility product constants of some combinations. For example, mixing potassium phosphate with sodium chloride imposes a risk of precipitating sodium phosphate salts which are much less soluble than potassium phosphate salts. Mixing potassium phosphate with potassium chloride suspends this risk. In a similar example, mixing high concentrations of ammonium sulfate and sodium chloride risks precipitation of less soluble sodium sulfate. The problem does not occur if ammonium sulfate is mixed with ammonium chloride or if sodium sulfate is mixed with sodium chloride. This caution does not suspend all combinations that have potential to create salt-solubility issues. It rather requires attention to the need for awareness to manage the issue if it proves to be problematical.

In some embodiments, the method of the invention may be performed at approximately neutral pH, where the term "approximately neutral pH" is understood to mean within the range of about pH 6.5 to about pH 7.5. In other embodiments, the entire method or different segment or buffers of the method may be performed a pH value from a broader range, such as from pH 6.0 to pH 8.0, or pH 5.5 to pH 8.5, or pH 5.0 to pH 9.0, or pH 4.0 to pH 9.0. Persons of experience in the art will recognize that the use of ammonium salts at a pH greater than 7.0 is discouraged because the ammonium ions convert spontaneously to ammonia gas which creates buffer instability, may pose a safety hazard, and may damage the desired DNA plasmid.

In some embodiments, it is not required that the neutral salt be present during the original binding of the pDNA to the HIC column. The key requirement is that it be present with the kosmotropic salt during elution of the DNA. In one embodiment, the pDNA may be bound in only the first kosmotropic salt and the neutral salt may be introduced in a subsequent step so that it is present during elution of the DNA plasmid.

In some embodiments, the concentration of the kosmotropic salt is reduced gradually while maintaining the concentration of the neutral salt constant. Gradual reduction of the first salt results in formation of a so-called linear gradient, and more specifically of a descending linear gradient. In some embodiments, the concentration of the kosmotropic salt is reduced in increments while maintaining the concentration of the neutral salt constant. Incremental reduction results in formation of a so-called step gradient, and more specifically of a descending step gradient. In some embodiments, the elution gradient may include step segments and linear segments.

In some embodiments the concentration of the neutral salt may be varied during performance of the method.

In some embodiments, the method may be configured so that pDNA is bound in the presence of a buffer containing only the kosmotropic salt, and the gradient endpoint buffer contains only the neutral salt. In such a configuration, simple math highlights that the concentration of the second salt in the gradient endpoint buffer must be high enough so that it reaches the threshold concentration of second salt required to maintain binding of RNA, proteins, and DNA-protein-RNA aggregates as the pDNA elutes. In one such embodiment, where the concentration of the first salt in the pDNA binding buffer is 2 M, and the concentration of the second salt in the gradient endpoint buffer is 4 M, as the first salt descends to a concentration of 1 M, the concentration of the second salt ascends to a concentration of 2 M. This approach of forming gradients where one component is concentrated in the starting buffer and a different component is concentrated in the endpoint buffer is known in the art as a crossed gradient.

In a related embodiment using the crossed gradient approach, the binding buffer containing the kosmotropic salt may contain a neutral salt, where the concentration of the neutral salt in the binding buffer is different than the concentration of the neutral salt in the gradient endpoint buffer. In one such embodiment, the concentration of the second salt in the gradient start buffer is lower than its concentration in the gradient endpoint buffer. In other embodiments, the gradient endpoint buffer may contain a lesser concentration of the kosmotropic salt than the concentration of the kosmotropic salt in the gradient start buffer.

In some embodiments, the column may be regenerated by a cleaning step as soon as the desired pDNA is eluted. In some such embodiments, the formulation of the cleaning step may be 1 M NaOH, or a lesser concentration of NaOH, or a greater concentration of NaOH, or 1 M NaOH plus 2 M NaCl, or 500 mM NaOH plus 3 M NaCl, or some other combination of NaOH and NaCl, or some combination of KOH and KCl. Cleaning solutions may also include a chelating agent such as ethylenediaminetetraacetic acid (EDTA) in a concentration ranging from 1 mM to 100 mM. In some embodiments, after elution of the DNA plasmid, a second elution may be performed in which the concentration of the neutral salt is reduced in order to recover the contaminants. In one such embodiment, the second elution may be conducted in a single step so that the contaminants are concentrated to facilitate their analysis. In another such embodiment, the second elution may be conducted as multi-step or linear gradient to evaluate the relative retention of various contaminants.

In some embodiments where the objective is to concentrate the pDNA while removing small molecule contaminants, RNA, host cell DNA-protein-RNA, and protein contaminants, and knowingly sacrifice the ability of the first salt to fractionate supercoiled pDNA from open-circular pDNA, the pDNA may be eluted in a step to reduce or eliminate the kosmotropic salt while maintain the presence of the neutral salt.

In some embodiments the sample may be prepared for application to the HIC column by first exposing it to a neutral salt for the purpose of precipitating a portion of the contaminants. To the extent that such precipitates are formed, they can be removed in advance of adding the first kosmotropic salt to the sample prior to binding the sample to the HIC column.

In some embodiments, the sample may be prepared for application to the HIC column by first exposing it to a neutral salt in the presence of hydrophobic particles, so that proteins, RNA, and DNA-protein-RNA contaminants bind to the particles to aid their sedimentation. In one such embodiment, the neutral salt may be lithium chloride or calcium chloride. It will be recognized by persons of knowledge in the art of plasmid DNA purification that this can replace the common practice of performing precipitation with calcium chloride to reduce RNA contamination or be used in combination with calcium precipitation to more effectively remove proteins, RNA, and DNA-protein-RNA aggregates in advance of a first chromatographic purification step.

In one embodiment, the sample preparation method is performed a hydrophobic surface other than loose particles. In one such embodiment, the sample preparation method is performed with a hydrophobic depth filtration device, or another device housing a hydrophobic surface or surfaces, potentially including a column packed with porous hydrophobic particles or nanofibers. In one embodiment following sample preparation by treatment with a neutral salt in the presence of a hydrophobic surface, a kosmotropic salt may be subsequently added to the treated sample in preparation for performing the method of the invention. In another embodiment following sample preparation by treatment with a neutral salt in the presence of a hydrophobic surface, the sample may be subsequently diluted with water or a low-conductivity buffer to prepare the sample for anion exchange chromatography. In another embodiment following sample preparation by treatment with a neutral salt in the presence of a hydrophobic surface, the sample may be equilibrated for another type of processing.

In some embodiments, the method of the invention is performed as a first chromatography step in a process for purification of plasmid DNA. In other embodiments, the method of the invention is performed as a second or later chromatography step in a process for purification of plasmid DNA.

In some embodiments, the method of the invention is followed by an anion exchange chromatography step. In other embodiments, the method of the invention is preceded by an anion exchange chromatography step. In another embodiment, the method of the invention is combined with a metal affinity chromatography step. In another embodiment, the method of the invention is combined with another chromatography step. In another embodiment, the method of the invention is combined with more than one additional chromatography step. In one such embodiment the method of the invention is combined with an anion exchange chromatography step and a metal affinity chromatography step. In another such embodiment, the method of the invention is combined with an anion exchange or metal affinity chromatography step and another chromatography step. In any of the above embodiments, and additional chromatography step may be a size exclusion chromatography step. In other embodiments, the method of the invention may be the only chromatography step.

It will be recognized by persons of skill in the art that RNA contamination of pDNA preparations is diverse. It may contain RNA of a wide range of sizes, and the RNA will commonly be strongly associated with proteins, producing complexes with chromatographic behavior distinct from purified RNA. The method of the invention will particularly enhance removal of large RNA, RNA-protein complexes, and RNA-protein-DNA complexes. Populations of very small RNA may elute during reduction of the kosmotropic salt to elute DNA, but this population of RNA will be reduced more effectively by anion exchange chromatography than the RNA that contaminants pDNA when HIC is performed under the usual traditional conditions of eluting with a simple kosmotropic salt gradient.

REFERENCES

All references cited herein are incorporated by reference to the full extent to which the incorporation is not inconsistent with the express teachings herein.

[1] C Schafer-Nielsen, C Rose, Separation of nucleic acids and chromatin proteins by hydrophobic interaction chromatography, Biochim Biophys Acta 696 (1982) 323-331.

[2] W Melander, C Horvath, Salt effects on hydrophobic interactions in precipitation and chromatography of proteins: an interpretation of the lyotropic series, Arch Biochem Biophys 183 (1977) 200-215.

The invention is further explained by the following non-limiting examples.

EXAMPLES

Example 1

Removal of Protein, RNA, DNA-Protein-RNA Aggregates, and Low Molecular Weight Contaminants from a Plasmid DNA Preparation A butyl monolith for HIC is equilibrated to a combination of 50 mM Hepes, 1.8 M ammonium sulfate, 1.8 M NaCl, 10 mM EDTA, pH 7.0. A sample containing an *E. coli* lysate that has been processed by calcium chloride precipitation and filtration of the supernatant is titrated to pH 7.0 and ammonium sulfate is added to a final concentration of 1.8 M. The sample is applied to the column and the column is washed with equilibration buffer to displace unbound low molecular weight contaminants. The plasmid DNA is then eluted in a linear gradient of descending ammonium sulfate concentration while the concentration of sodium chloride is held constant. See FIG. 1 (ft: flow through, sc: supercoiled, oc: open-circular).

Example 2

Binding and Elution of Double-Stranded DNA

Figure 2:
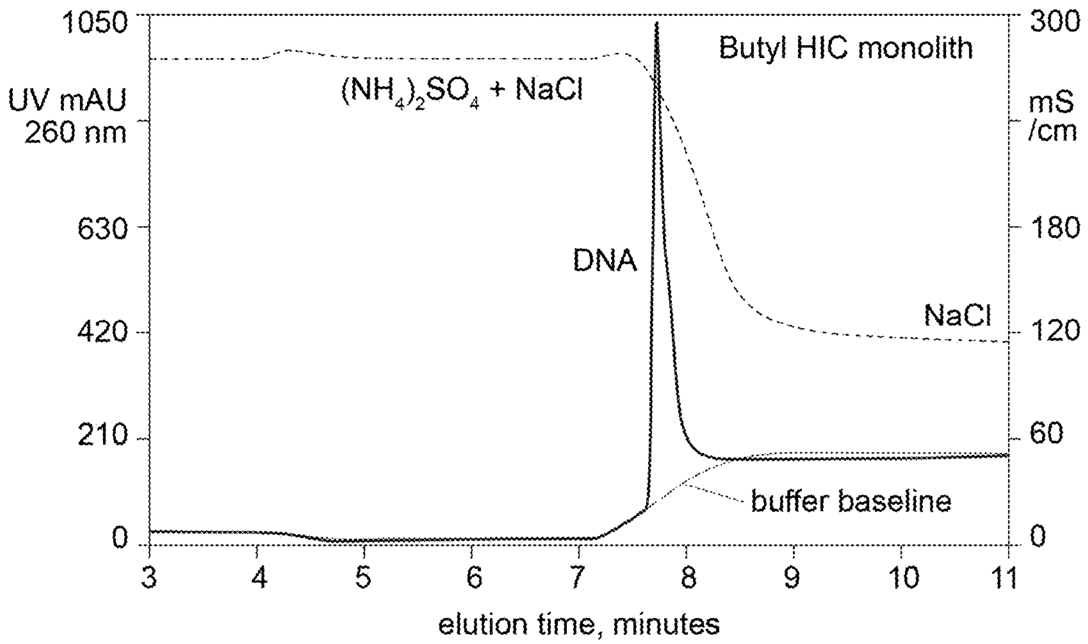
FIG. 2 depicts elution of DNA in the gradient of the kosmotropic salt.

A sample containing double-stranded DNA of different sizes ranging from 80 base pairs to 10,000 base 10,000 base pairs was applied to a high density butyl (HIC) monolith in 50 mM Tris pH, 10 mM EDTA, 2.5 M ammonium sulfate, pH 7.2. The loaded column was re-equilibrated to 50 mM Tris, 10 mM EDTA, 2.5 M ammonium sulfate, 1.2 M sodium chloride, pH 7.2. The column was then eluted with a linear gradient to 50 mM Tris pH, 10 mM EDTA, 1.2 M sodium chloride, pH 7.2. Double-stranded DNA eluted in the gradient. See FIG. 2.

Example 3

Binding and Non-Elution of Single-Stranded RNA

The conditions of example 1 were repeated except with a sample containing single-stranded RNA of different sizes ranging from 200 bases to 6,000 bases. The RNA failed to elute in the gradient of descending ammonium sulfate and remained bound to the column in NaCl.

Example 4

Figure 3:
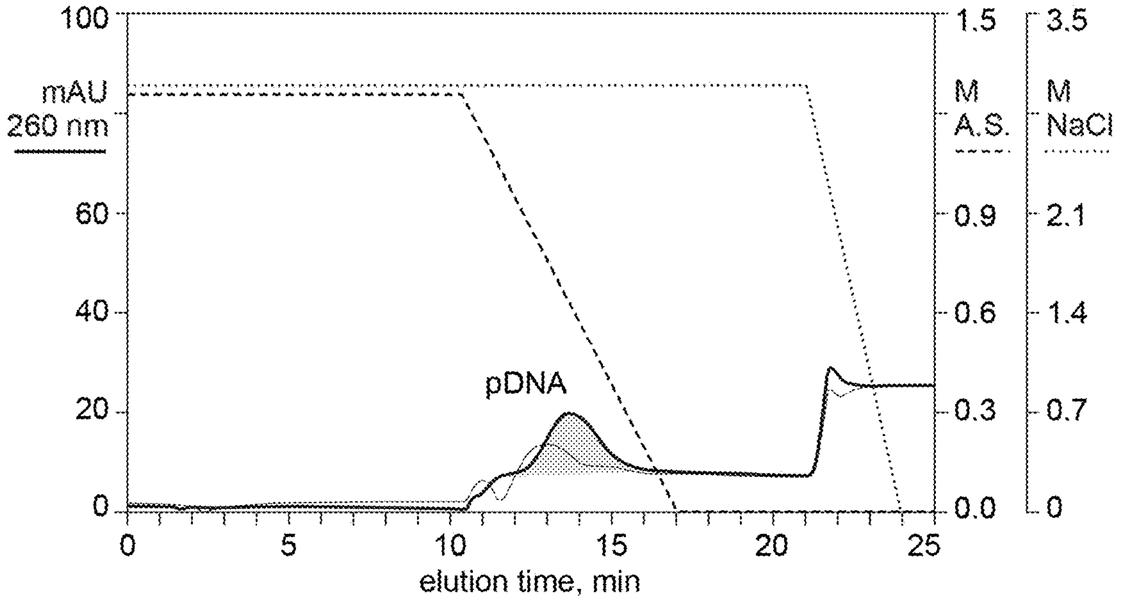
FIG. 3 depicts elution of plasmid DNA in the gradient of the kosmotropic salt while the concentration of a neutral salt is held constant.

Elution of pDNA from a HIC column by reducing the concentration of a kosmotropic salt while the concentration of a neutral salt is held constant. A binding buffer concentrate (buffer A) was prepared containing 50 mM Hepes, 1.25 M sodium sulfate, 3.0 M sodium chloride, pH 7.2. A pDNA elution buffer (buffer B) was prepared containing 50 mM Hepes, 3.0 M sodium chloride, pH 7.2. An RNA elution buffer (buffer C) was prepared containing 50 mM Hepes, pH 7.2. A 100 μL butyl monolith was equilibrated at a flow rate of 0.5 mL/min with a mixture of 90% buffer A and 10% buffer B. A purified DNA plasmid of about 4.7 kbp was loaded onto the column, which was then washed for 10 min with equilibration buffer. The pDNA was then eluted with a 4 min linear gradient to buffer B. Buffer B was flowed through the column for an additional 4 min. Buffer composition was then switched to buffer C and continued for an additional 7 min. Results are illustrated in FIG. 3. The pDNA bound to the column under equilibration conditions, it remained bound in the wash. It eluted in the gradient to buffer B. The fine solid line represents the buffer baseline.

Example 5

Figure 4:
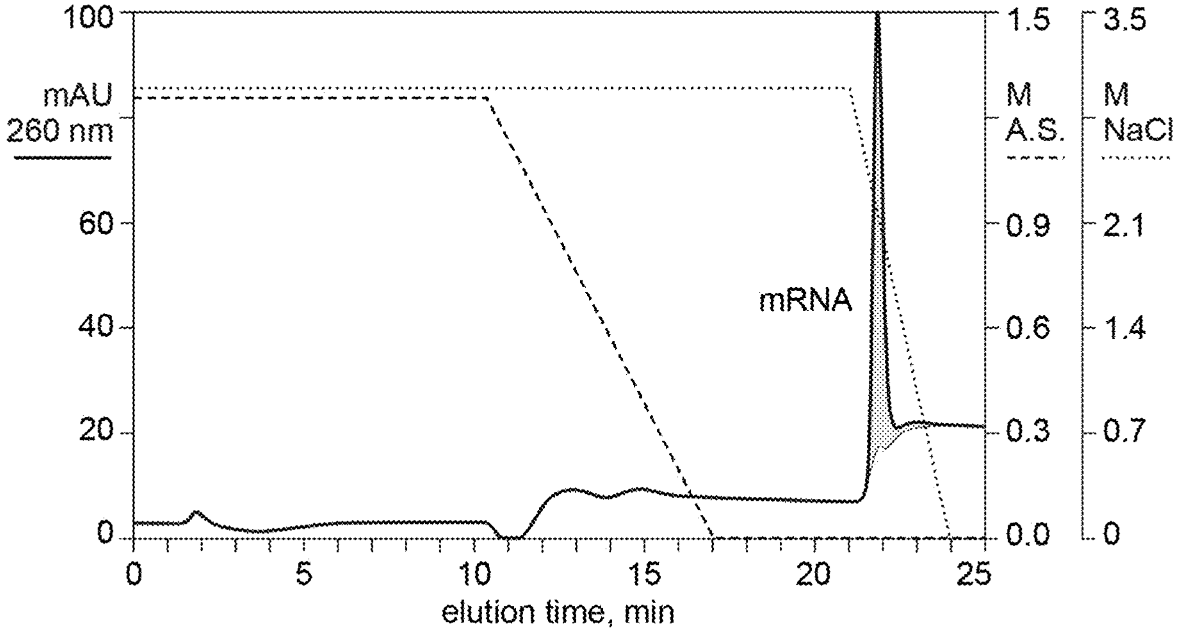
FIG. 4 depicts the elution behavior of RNA, which remains bound while the concentration of a kosmotropic salt is reduced and the concentration of a neutral salt is held constant, and which elutes when the concentration of the neutral salt is reduced.

Retention of RNA by a HIC column while the concentration of a kosmotropic salt is reduced and the concentration of a neutral salt is held constant, then subsequent elution of the RNA by reducing the concentration of the neutral salt. The conditions of Example 4 were reproduced except using a sample consisting of mRNA with a length of 4400 nucleotides. Results are illustrated in FIG. 4. The mRNA bound to the column under equilibration conditions, it remained bound in the wash. It remained bound in the gradient to buffer B and the subsequent wash in buffer B. It eluted in the step to buffer C. The fine solid line represents the buffer baseline.

Example 6

Figure 5:
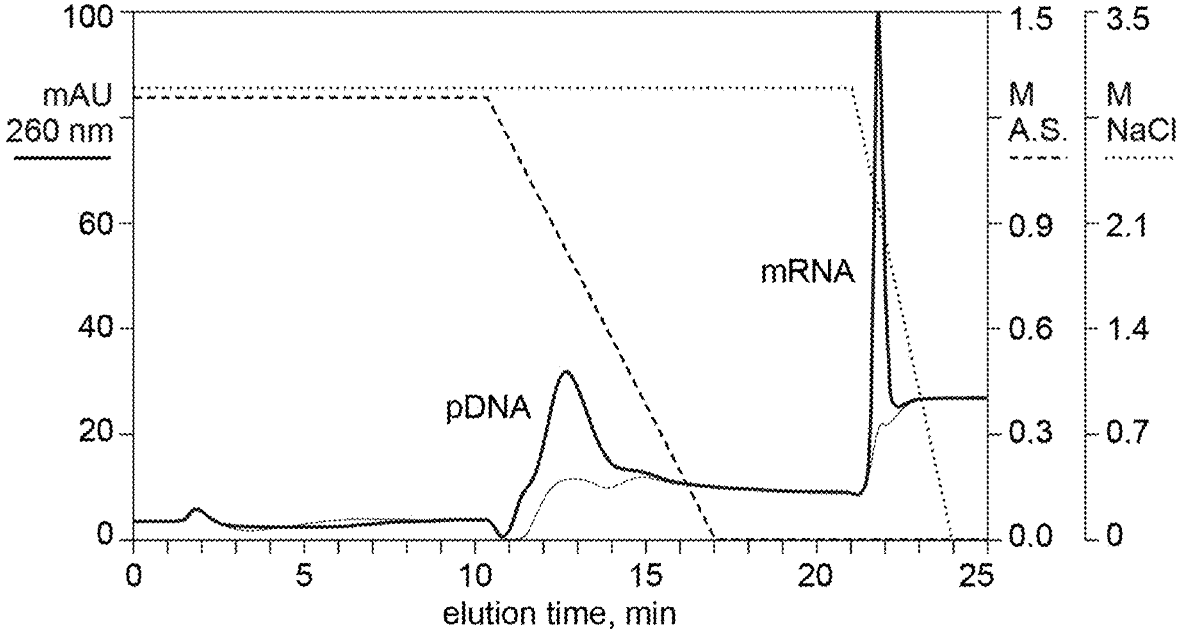
FIG. 5 depicts the respective elution behaviors of plasmid DNA and RNA, where the pDNA elutes in a reducing gradient of the kosmotropic salt while the concentration of a neutral salt is held constant, and the RNA elutes when the concentration of the neutral salt is reduced.

Elution of pDNA from a HIC column by reducing the concentration of a kosmotropic salt while the concentration of a neutral salt is held constant, followed by elution of the RNA by reducing the concentration of the neutral salt. The conditions of Example 3 were reproduced except using a sample consisting of pDNA with a length of 4.7 kbp mixed with mRNA with a length of 4400 nucleotides. Results are illustrated in FIG. 5. The pDNA eluted as in Example 4. The mRNA eluted as in example 5. The fine solid line represents the buffer baseline.

Given that the objective of the method of the invention is to produce a more highly purified pDNA fraction, it will be understood that a second elution step of reducing the neutral salt concentration is included in the above examples mainly to illustrate the point that kosmotropic and neutral salt concentrations can be manipulated individually to gain control over different types of nucleic acids and their derivatives. In manufacturing circumstances, there would be little or no value in obtaining the contaminants eluted by reducing the concentration of the neutral salt. It would shorten and simplify the process to go directly to a cleaning step with sodium hydroxide.

The invention claimed is:

1. A method for manufacturing a purified plasmid DNA (pDNA) preparation from a sample comprising pDNA and a contaminant, the method comprising the steps of:

Contacting the sample with a hydrophobic interaction chromatography (HIC) material in a solution comprising a neutral salt and a kosmotropic salt in a concentration which forces the pDNA and the contaminant to adsorb on the HIC material, wherein the kosmotropic salt is selected from the group consisting of ammonium sulfate, sodium sulfate, potassium phosphate, sodium citrate, potassium citrate, and combinations thereof, and wherein the concentration of the neutral salt is in the range of from 1.0 M to 5.0 M;

Subsequent to adsorbing of the pDNA on the HIC material, eluting with an elution fluid with reduced concentration of the kosmotropic salt relative to the concentration in the step of contacting the sample while having a continued presence of the neutral salt at an appropriate concentration range, such that the pDNA desorbs from the HIC material and the contaminant stays adsorbed to the HIC material by the continued presence of the neutral salt; and Obtaining the purified pDNA preparation.

2. The method of claim 1 wherein the concentration of the kosmotropic salt is from 1.0 M to 2.5 M in the step of contacting the sample.

3. The method of claim 1 wherein the neutral salt is selected from the group consisting of sodium chloride, potassium chloride, lithium chloride, ammonium chloride, sodium acetate, potassium acetate, lithium acetate, ammonium acetate, and combinations thereof.

4. The method of claim 1 wherein the sample is a lysate of prokaryotic cells containing plasmid DNA.

5. The method of claim 1 wherein the contaminant is selected from the group consisting of proteins, RNA, RNA-protein aggregates, DNA-protein aggregates, and DNA-protein-RNA aggregates.

6. The method of claim 1 wherein the HIC material is a polymer bearing a hydrophobic ligand.

7. The method of claim 6 wherein the hydrophobic ligand is an aromatic ligand or an alkyl ligand or combinations thereof.

8. The method of claim 1 wherein the HIC material is arranged in a chromatographic column.

9. The method of claim 1 wherein the concentration of the neutral salt is unchanged during the step of contacting the sample and the step of eluting with reduced concentration of the kosmotropic salt.

10. The method of claim 1 wherein a further chromatography step is used before or after the hydrophobic interaction chromatography.

11. The method of claim 10 wherein the further chromatography step is anion exchange chromatography.

12. The method of claim 7 wherein the aromatic ligand is a phenyl ligand, a benzyl ligand or combinations thereof.

13. The method of claim 7 wherein the alkyl ligand is a butyl ligand, a hexyl ligand, an octyl ligand or combinations thereof.

14. The method of claim 1 wherein the concentration of the kosmotropic salt is from 1.7 M to 1.9 M in the step of contacting the sample.

15. The method of claim 1 wherein the concentration of the kosmotropic salt is from 1.5 M to 2.0 M in the step of contacting the sample.

16. The method of claim 1 wherein the concentration of the neutral salt is in the range of from 1.5 M to 2.0 M in the step of contacting the sample.

17. The method of claim 1 wherein the concentration of the neutral salt is in the range of from 1.25 M to 2.5 M in the step of contacting the sample.

18. The method of claim 1 wherein the concentration of the neutral salt is in the range of from 1.0 M to 3.0 M in the step of contacting the sample.

* * * * *